United States Patent
Miller et al.

(10) Patent No.: US 10,646,213 B2
(45) Date of Patent: May 12, 2020

(54) REMOTE SPINAL MANIPULATING ASSEMBLY AND METHOD FOR REMOTE SPINAL MANIPULATION

(71) Applicant: Warsaw Orthopedic, Inc, Warsaw, IN (US)

(72) Inventors: Keith E. Miller, Germantown, TN (US); Richard Quinn Brown, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 386 days.

(21) Appl. No.: 15/383,795

(22) Filed: Dec. 19, 2016

(65) Prior Publication Data

US 2018/0168565 A1    Jun. 21, 2018

(51) Int. Cl.
*A61B 17/02* (2006.01)
*A61B 17/70* (2006.01)
*A61B 17/00* (2006.01)

(52) U.S. Cl.
CPC ........ *A61B 17/025* (2013.01); *A61B 17/7077* (2013.01); *A61B 2017/00212* (2013.01); *A61B 2017/0256* (2013.01)

(58) Field of Classification Search
CPC ....... A61B 17/02; A61B 17/025; A61B 17/70; A61B 17/7074
See application file for complete search history.

(56) References Cited

U.S. PATENT DOCUMENTS

| | | | |
|---|---|---|---|
| 6,146,386 A | * | 11/2000 | Blackman .......... A61B 17/7079 606/103 |
| 8,105,329 B2 | | 1/2012 | Brumfield et al. |
| 8,235,998 B2 | | 8/2012 | Miller et al. |
| 8,491,588 B2 | | 7/2013 | Wall et al. |
| 8,828,059 B2 | | 9/2014 | Steele et al. |
| 9,289,250 B2 | | 3/2016 | Wall et al. |
| 9,387,018 B2 | | 7/2016 | Brown et al. |
| 2002/0123754 A1 | | 9/2002 | Holmes et al. |

(Continued)

OTHER PUBLICATIONS

International Search Report for PCT PCT/US2017/066981 dated Apr. 13, 2018 (2 pages).

*Primary Examiner* — Christopher J Beccia

(57) ABSTRACT

An assembly for remotely manipulating a patient's spine. A compressor/distractor mechanism attaches to spinal anatomy or vertebral screws on adjacent vertebrae at a spinal surgical site on a patient's spine. A flexible cable is operatively connected to the compressor/distractor mechanism and to a control mechanism. The control mechanism manipulates the flexible cable, controlling the compressor/distractor mechanism to compress or distract the vertebrae. A rotatable surgical table with a remote control can be used in place of the compressor/distractor mechanism and the control mechanism. The rotatable surgical table can rotate the patient to place the spinal surgical site in a desired compressed or distracted position, and to place the patient in a desired orientation with respect to a horizontal reference plane. The assembly permits manipulation of the spine at the surgical site via a posterior approach, while the surgeon can also manipulate the spine at the surgical site via an anterior, lateral or oblique approach.

20 Claims, 12 Drawing Sheets

(56) References Cited

U.S. PATENT DOCUMENTS

| | | | |
|---|---|---|---|
| 2011/0184245 A1* | 7/2011 | Xia | A61B 17/0206 600/202 |
| 2011/0257655 A1 | 10/2011 | Copf, Jr. | |
| 2012/0316609 A1* | 12/2012 | Wall | A61B 17/7079 606/86 A |
| 2013/0289633 A1 | 10/2013 | Gleeson et al. | |
| 2014/0336711 A1 | 11/2014 | Steele et al. | |
| 2014/0358150 A1 | 12/2014 | Kaufman et al. | |
| 2016/0038189 A1 | 2/2016 | Wall et al. | |

* cited by examiner

REMOTE SPINAL MANIPULATING ASSEMBLY AND METHOD FOR REMOTE SPINAL MANIPULATION

BACKGROUND OF THE INVENTION

Field of the Invention

The present invention relates to an apparatus for remotely manipulating a patient's spine, and a method for remotely manipulating the patient's spine, for example while performing simultaneous access or multi-access spinal surgery. More specifically, the present invention relates to an apparatus and method that allows a surgeon to manipulate the patient's spine at a surgical site using an approach, to which the surgeon has remote access, while simultaneously allowing the surgeon to manipulate the patient's spine at the surgical site using another approach, to which the surgeon has direct access.

Description of the Related Art

Manipulation of a patient's spine at a surgical site, from a location to which the surgeon does not have direct access to the surgical site, is known. For example, in some instances a surgeon may need to operate on a patient's spine using, e.g., a posterior approach to the spine, while the surgeon is located at, e.g., an anterior side of the patient, or an anterior approach to the spine. Alternately, the surgeon may need to operate on the patient's spine using, e.g., an anterior approach to the spine while the surgeon is located at, e.g., the posterior side of the patient. Alternately, the surgeon may need to manipulate the posterior side of the patient's spine using a posterior approach, while simultaneously manipulating the anterior side of the spine using an anterior approach, an oblique approach, or a side approach. Existing devices and methods do not allow surgeons to efficiently and safely compress or distract the posterior side of the spine while being located at the anterior side of the spine or at another side of the spine. Existing devices and methods do not allow a surgeon to simultaneously manipulate the anterior side of the spine and the posterior side of the spine. Likewise, existing devices and methods do not allow a surgeon to efficiently and safely manipulate the patient's spine using, e.g., a posterior approach, an anterior approach, a lateral approach, or an oblique approach to the spine, while the surgeon is located proximate another portion of the spine. In addition, existing devices and methods do not allow precise control of vertebral orientation during simultaneous manipulation of both the anterior and posterior aspects of the spine.

An apparatus and a method for remotely manipulating the spine are desirable, which allow for simultaneous manipulation of the anterior and posterior spine, allow for improved control of vertebral orientation, allow for improved distribution of forces being applied to the spine; and allow the surgeon to manipulate the spine without losing focus on his current access point.

The present invention seeks to address these and other shortcomings in the related art.

SUMMARY OF THE INVENTION

In one embodiment of the invention, an assembly for remotely manipulating a patient's spine at a surgical site in the patient is provided. The assembly includes a compressor/distractor mechanism having a proximal end and a distal end, the distal end being configured to be attached to one of spinal anatomy and vertebral screws located on adjacent vertebrae at the spinal surgical site on the patient. A flexible connection portion has a length, a proximal end, and a distal end, the distal end being operatively connected to the compressor/distractor mechanism. A control mechanism is operatively connected to the proximal end of the flexible connection portion. The control mechanism is configured to manipulate the flexible connection portion, thereby controlling the compressor/distractor mechanism to one of compress and distract the adjacent vertebrae at the spinal surgical site on the patient. The flexible connection portion enables the control mechanism to be located at one of a posterior side of the patient, an anterior side of the patient, and a right lateral side of the patient, spaced away from the location of the compressor/distractor mechanism at the spinal surgical site, which can be located, e.g., at one of the anterior side of the patient, a left lateral side of the patient, the posterior side of the patient, and so on.

In one embodiment of the invention, the control mechanism includes a hinged lever, which is configured, upon compression thereof, to move an inner cable relative to an outer cable in the flexible connection portion, thereby compressing the compressor/distractor mechanism and compressing the adjacent vertebrae. In this embodiment, the hinged lever is further configured, upon expansion thereof, to increase the length of the flexible connection portion, thereby distracting the compressor/distractor mechanism, and distracting the adjacent vertebrae.

In one embodiment of the invention, the compressor/distractor mechanism includes first and second elongated arms, each of the first and second elongated arms including proximal end portions connected together by the flexible connection portion, mineral portions are pivotally connected together by a pit pin, and the distal end portions configured to attach to the one of vertebral screws and spinal anatomy located on the adjacent vertebrae at the spinal surgical site. In this embodiment the distal end portions of the first and second elongated arms of the compressor/distractor mechanism are configured to attach to at least one of vertebral screws, lamina, posterior processes, and transverse processes, and vertebral bodies on the adjacent vertebrae at the spinal surgical site.

In one embodiment of the invention the flexible connection portion includes at least one of a cable, a hydraulic hose, a pneumatic hose, and an electric wire.

In an alternative embodiment of the invention, the control mechanism includes a remote control for remotely controlling the compressor/distractor mechanism. In this embodiment the remote control is adapted to provide feedback to a surgeon performing the simultaneous access or multi-access spinal surgery on the patient's spine, the feedback including at least one of a force being applied to the patient's spine, the strain being applied to vertebral screws, an amount of compression/distraction, and at least one impulse from a neural integrity monitor.

In an alternative embodiment, the compressor/distractor mechanism is replaced by a surgical table configured to adjust an orientation of the patient's spine, including compressing and distracting the patient's spine, and angulating a lower half of the patient's body relative to an upper half of the patient's body. In this embodiment, the surgical table also is configured to rotate, thereby providing a plurality of orientations of the patient relative to a horizontal reference plane, and further providing access to the spinal surgical site, using at least one of a posterior approach, an anterior approach, a lateral approach, and an oblique approach thereto.

DETAILED DESCRIPTION OF THE PREFERRED EMBODIMENTS

The exemplary embodiments of the apparatus and related methods of use disclosed are discussed in terms of an apparatus and method for remotely manipulating a patient's spine at a surgical site in a patient, and more particularly to an assembly used to manipulate the patient's spine, and a method for remotely manipulating the patient's spine at a spinal surgical site via one approach path, e.g., a posterior approach, while allowing the surgeon simultaneously to directly manipulate the patient's spine at the spinal surgical site via another approach path, e.g., an anterior approach, a distal approach, or an oblique approach.

Figure 1:
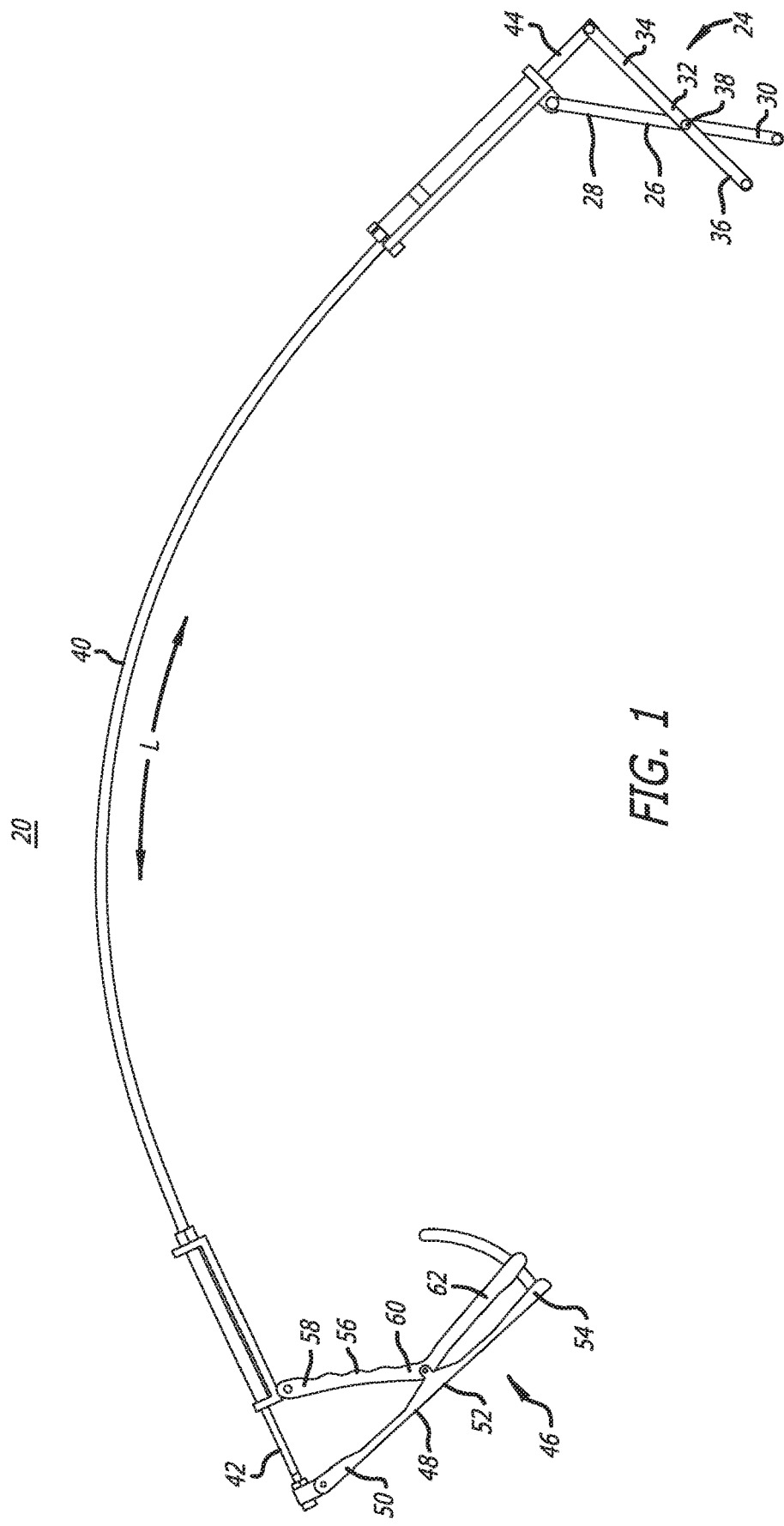
FIG. 1 is a perspective view of an apparatus in accordance with the invention for remotely manipulating a patient's spine.
Figure 4:
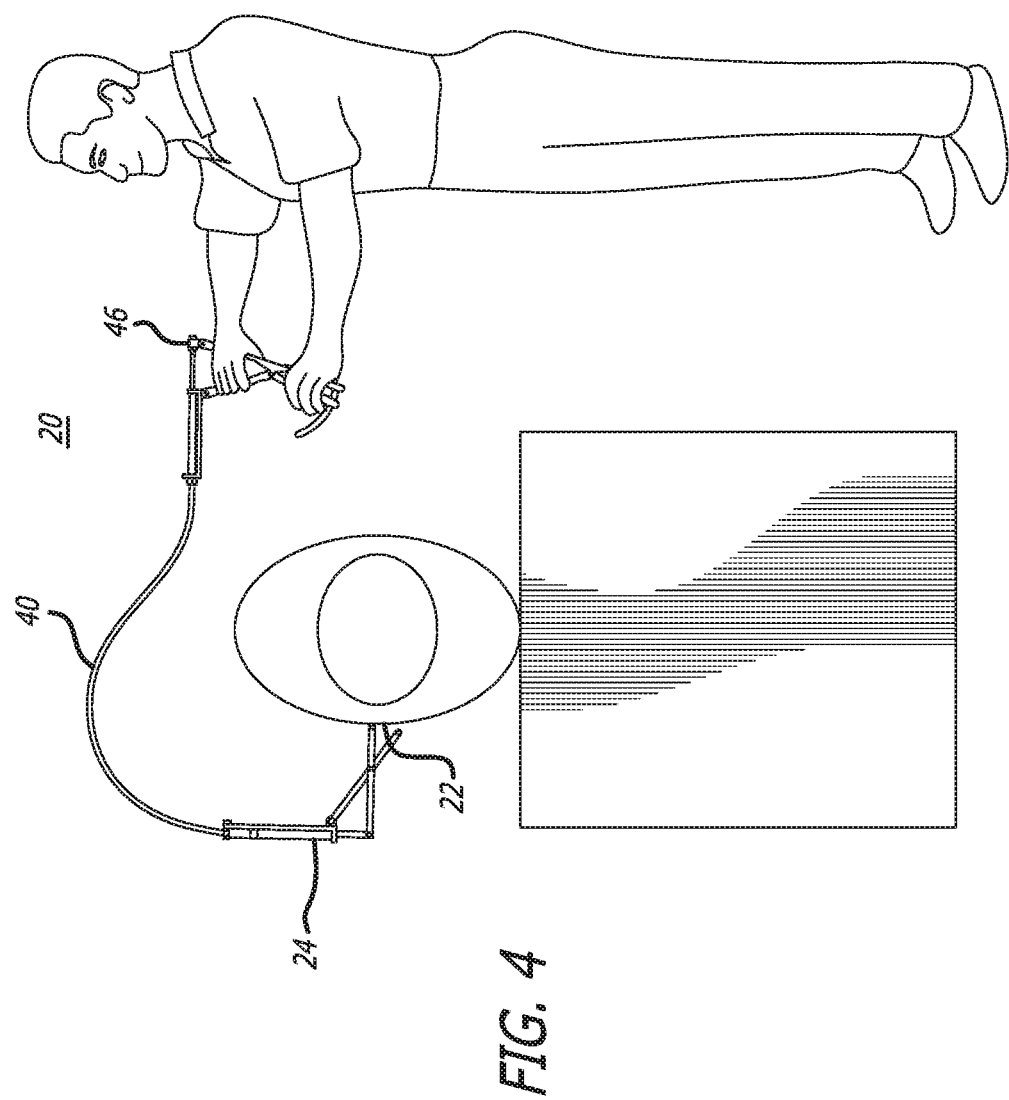
FIG. 4 is a schematic view of a surgeon manipulating a patient's spine, using an anterior approach while standing at a posterior side of the patient, using one embodiment of an apparatus in accordance with the invention for remotely manipulating a patient's spine.
Figure 5:
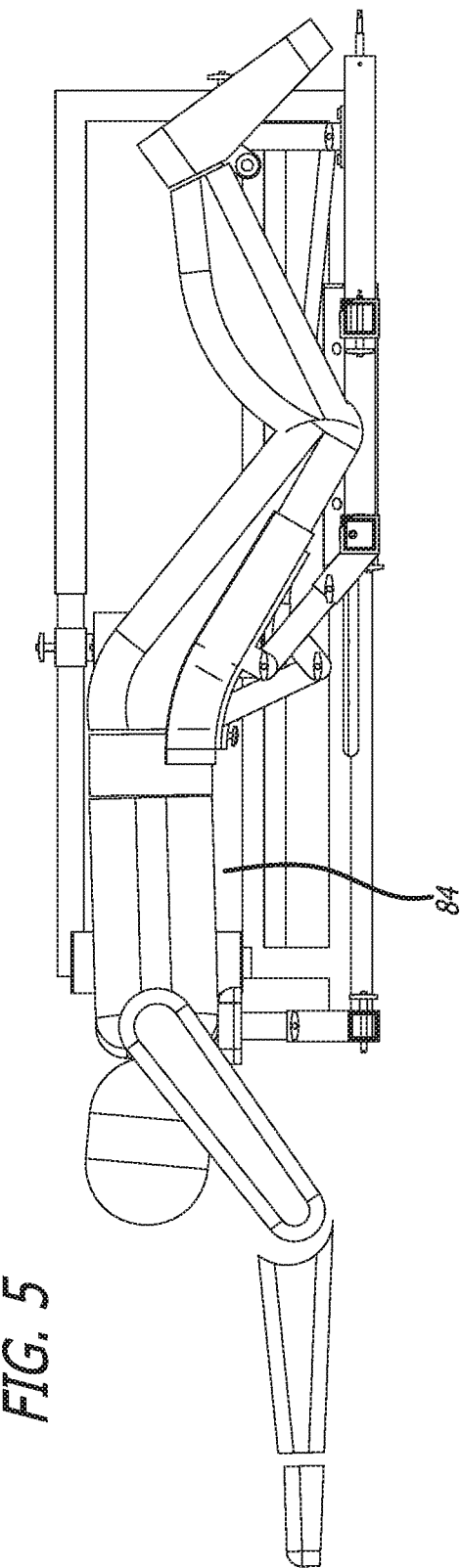
FIG. 5 is a side view of a surgical table used in an apparatus in accordance with the invention for remotely manipulating a patient's spine.
Figure 6:
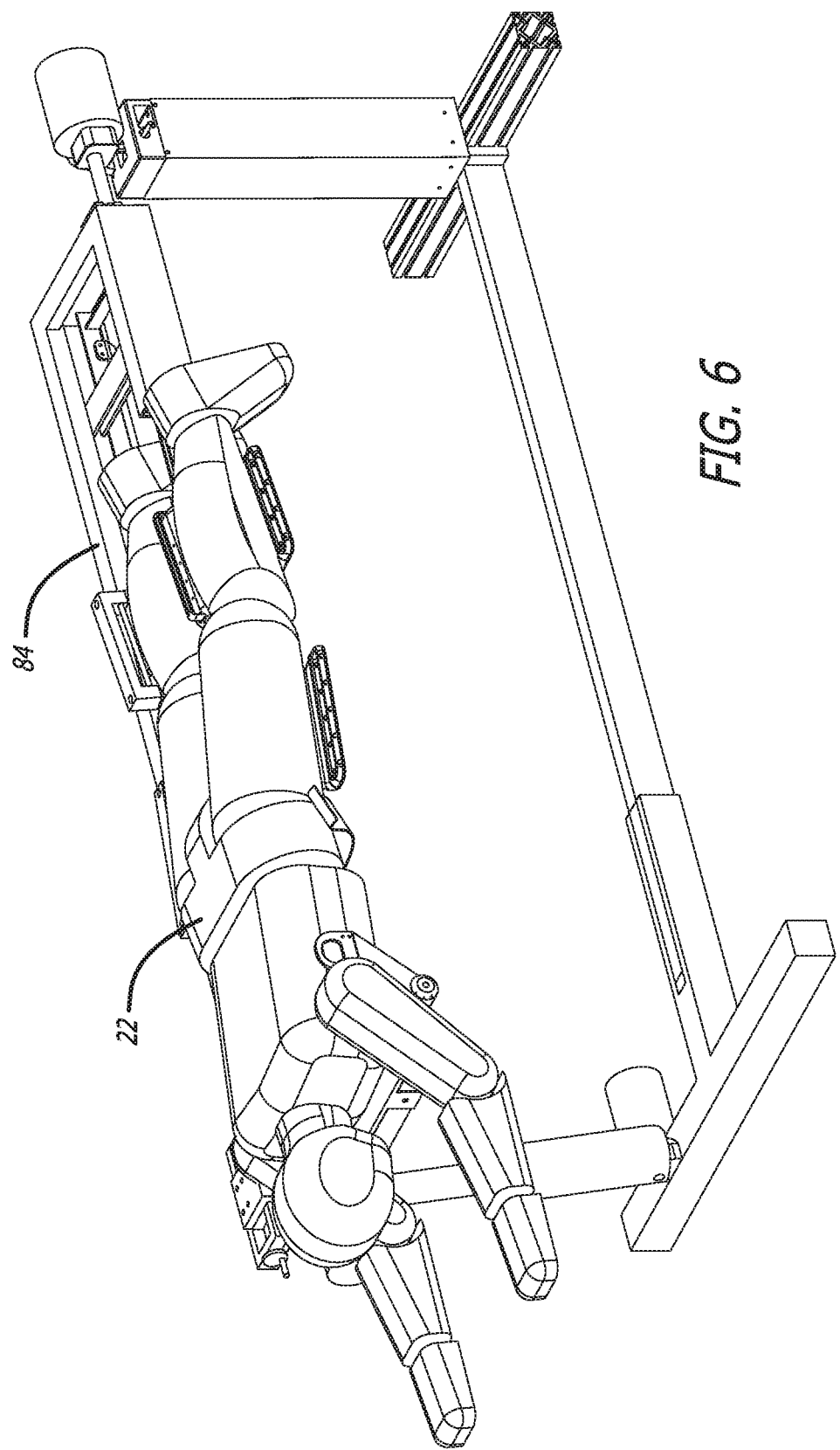
FIG. 6 is a perspective view of a surgical table used in an apparatus in accordance with the invention for remotely manipulating a patient's spine, depicting the table positioned to distract the patient's spine.
Figure 7:
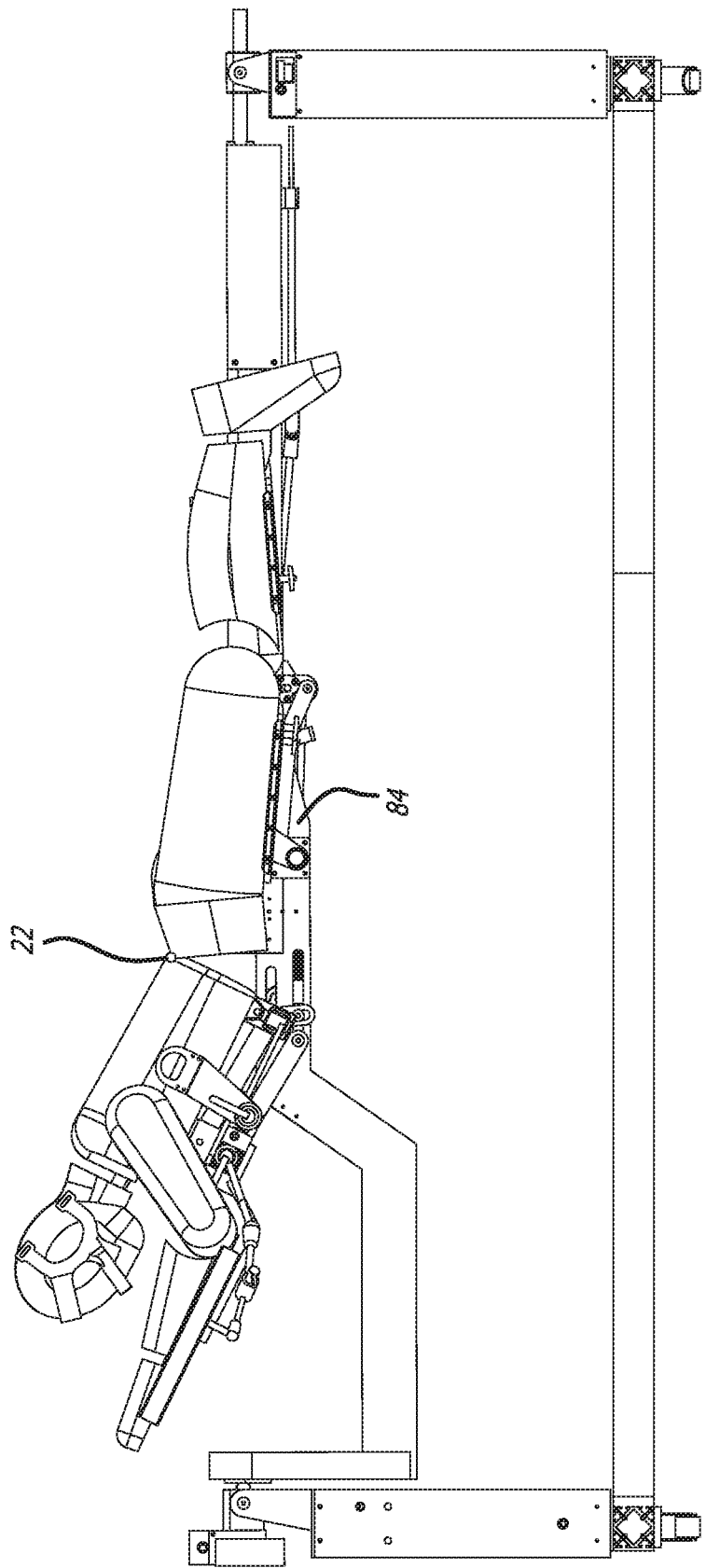
FIG. 7 is a side view of a surgical table used in an apparatus in accordance with the invention for remotely manipulating a patient's spine, depicting the table positioned to compress the patient's spine.
Figure 8:
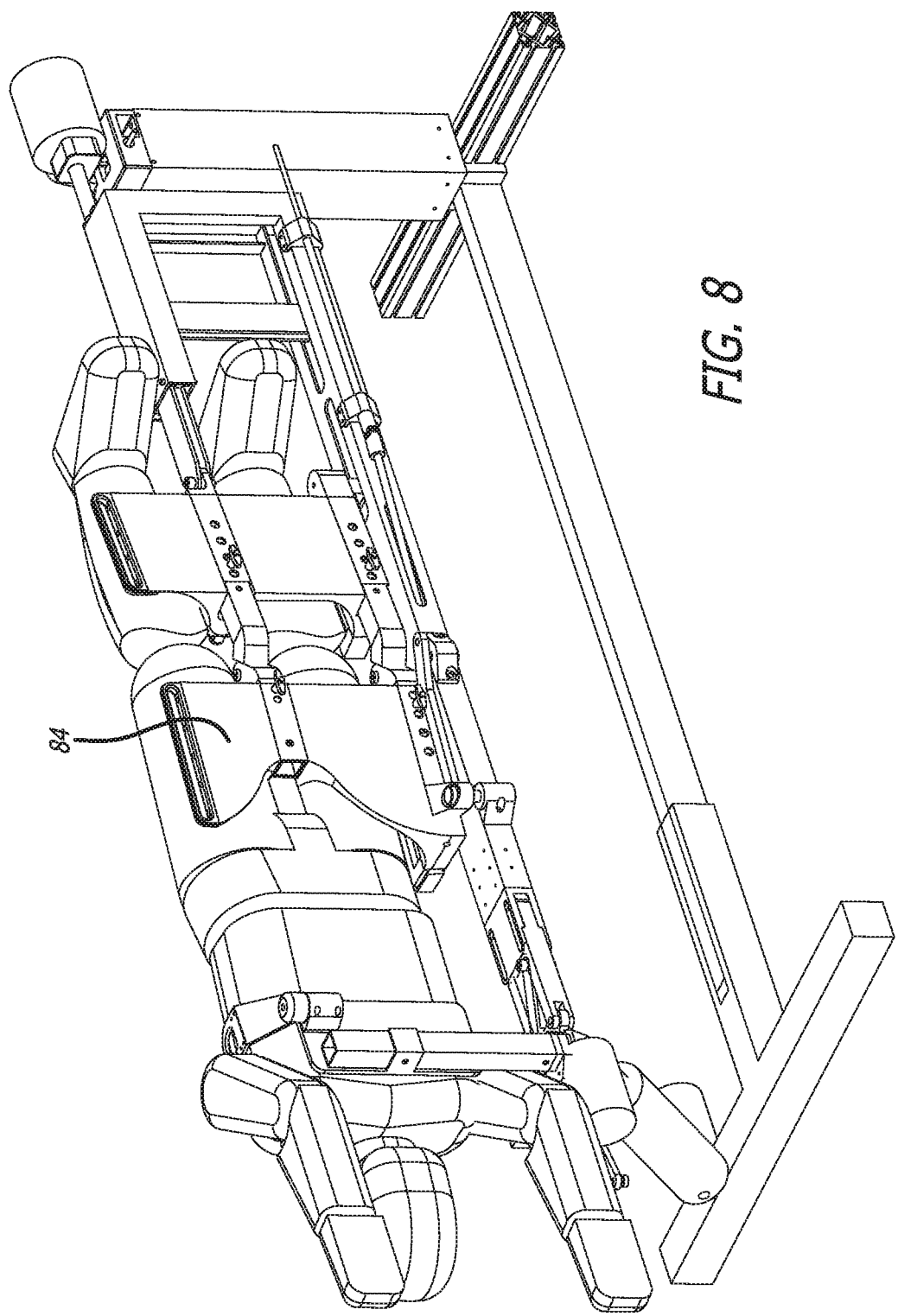
FIG. 8 is a side view of a surgical table used in an apparatus in accordance with the invention for remotely manipulating a patient's spine, depicting the table rotated to an orientation of the patient with respect to a horizontal plane.
Figure 9:
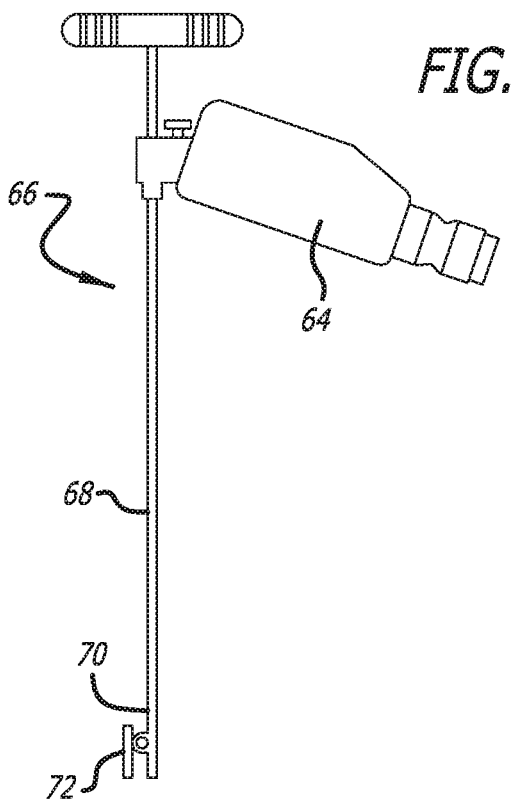
FIG. 9 is a side view of a radio frequency controller with an anterior compressor/distractor attached thereto.
Figure 10:
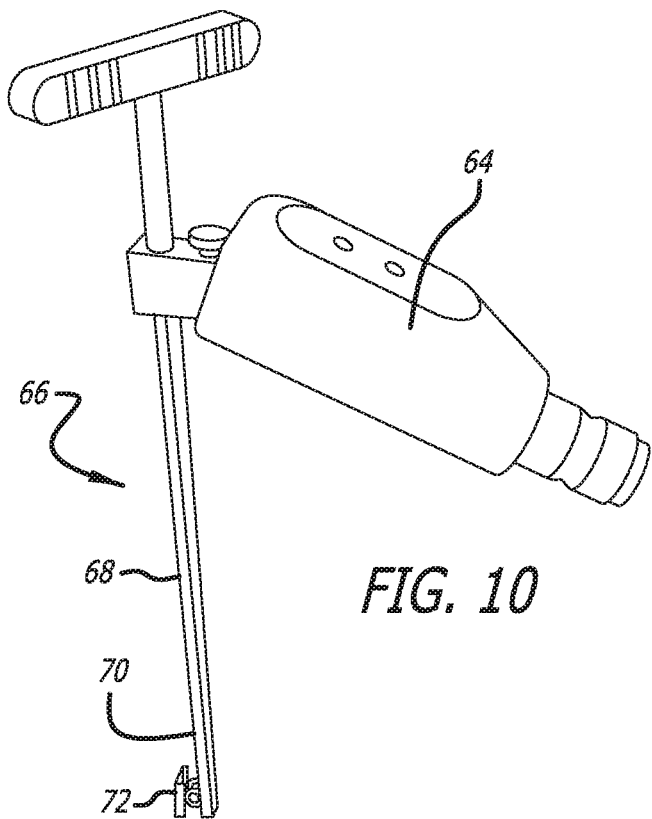
FIG. 10 is a perspective view of a radio frequency controller with an anterior compressor/distractor attached thereto.

In one preferred embodiment, a remote spinal manipulator 20 is configured for performing remote spinal manipulation at a spinal surgical site 22 on a patient's spine. Referring to FIGS. 1 and 4, remote spinal manipulator 20 is configured to allow a surgeon to remotely manipulate the spine at the spinal surgical site 22. Referring to FIG. 4, the remote spinal manipulator 20 accesses the spinal surgical site 22 via a posterior approach on the posterior side of the patient, while the surgeon is located at an anterior side of the patient.

Figure 2:
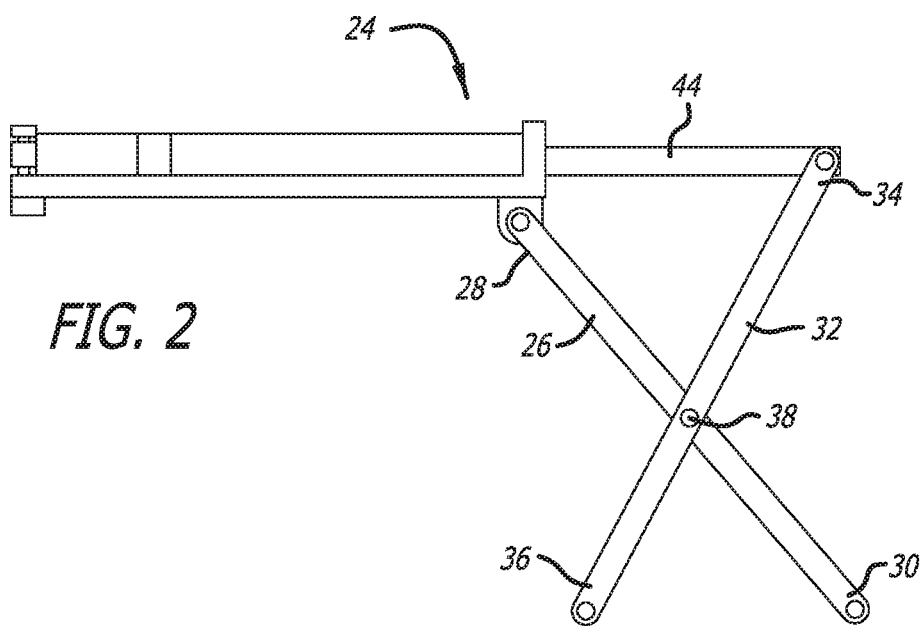
FIG. 2 is a side view of one embodiment of a compressor/distractor mechanism used in an apparatus in accordance with the invention for remotely manipulating a patient's spine.

In one preferred embodiment, the remote spinal manipulator 20 includes a compressor/distractor mechanism 24. Referring to FIGS. 1 and 2, the compressor/distractor mechanism 24 includes a first elongated arm 26 having a proximal end 28 and a distal end 30, and a second elongated arm 32 having a proximal end 34 and a distal end 36. The first and second elongated arms 26 and 32 are pivotally connected one to another approximately midway between the respective proximal and distal ends thereof by a pivot pin 38.

In one preferred embodiment, the remote spinal manipulator 20 includes a flexible connection portion 40. Referring to FIGS. 1 and 4, the flexible connection portion 40 has a length L1, a proximal end 42, and a distal end 44. Referring to FIG. 2, the distal end 44 connects together each of the distal ends 30 and 36 of the compressor/distractor mechanism 24. The flexible connection portion 40 may be a flexible cable, a flexible hydraulic hose, a flexible pneumatic hose, and a flexible electric wire. In another embodiment, instead of using a flexible connection portion 40, a radio-frequency communication device, a vibratory communication link, or an electro-magnetic communication link can be used to communicate the surgeon directions to the compressor/distractor mechanism 24.

In one preferred embodiment, the vibratory communication link may be a sonic link (not shown) or an ultra-sonic link (not shown). In one preferred embodiment, the electromagnetic communication link may be a light link (not shown) or a magnetic link (not shown).

Figure 3:
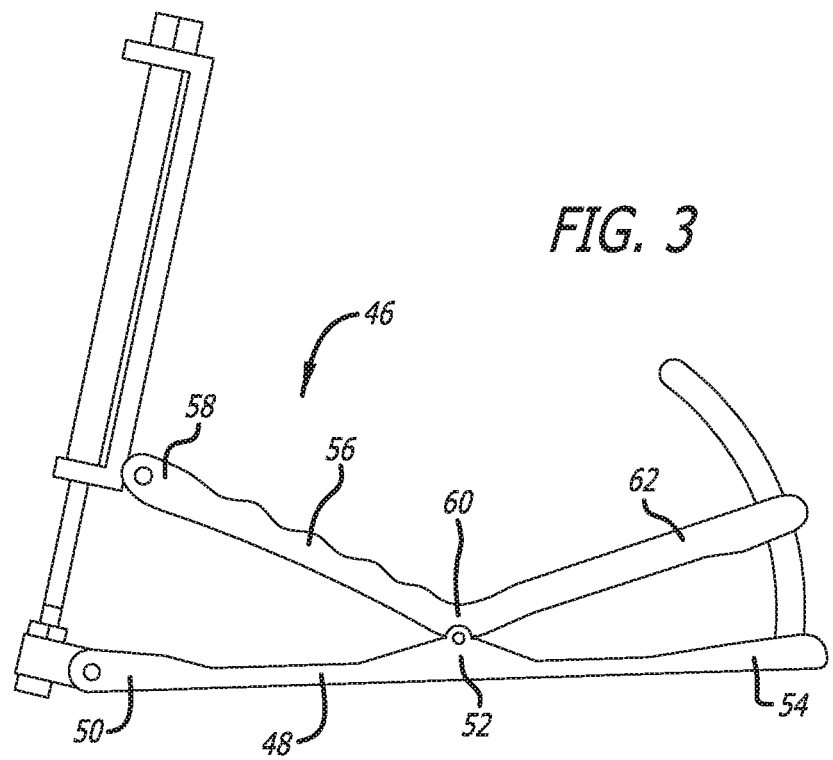
FIG. 3 is a side view of one embodiment of a control mechanism used in an apparatus in accordance with the invention for remotely manipulating a patient's spine.

In one preferred embodiment, the remote spinal manipulator 20 includes a control mechanism 46. Referring to FIGS. 1 and 3, the control mechanism 46 is configured as a hinged lever having a base portion 48 with a first end 50 connected to the proximal end 42 of the flexible connection portion 40, a central portion 52, and a second end 54. The control mechanism 46 further includes an upper portion 56 having a first end 58 connected to the flexible connection portion 40, a central portion 60 pivotally connected to the central portion 52 of the base portion 48, and a second end 62. Referring to FIG. 3, applying pressure to the first ends 50 and 58 of the control mechanism 46 causes the first end 50 of the base portion 48 and the first end 58 of the upper portion 56 to pivot toward one another about the central point 52, adding increased pressure to flexible connection portion 40, and moving an inner cable relative to an outer cable of the flexible connection portion 40. Moving the inner cable relative to the outer cable of the flexible connection portion 40 pulls together the first and second elongated arms 26 and 32, thereby resulting in compression of the adjacent vertebrae at the spinal surgical site with the compressor/distractor mechanism 24. Alternately, applying pressure to the second end 54 of the base portion 48 and the second end 62 of the upper portion 56 of the control mechanism 46, or else releasing pressure on the first ends 50 and 58, causes the second ends 54 and 62 to pivot toward one another about the central point 52, thereby reducing pressure on flexible connection portion 40, and increasing the length of the flexible connection portion 40. Increasing the length of the flexible connection portion 40 allows the first and second elongated arms 26 and 32 to move apart, resulting in distraction of the adjacent vertebrae at the spinal surgical site with the compressor/distractor mechanism 24. The pressures applied to the control mechanism 46 can be applied by hand by the surgeon, or may be applied via a remote radio frequency controller 64, discussed in detail below.

Figure 11:
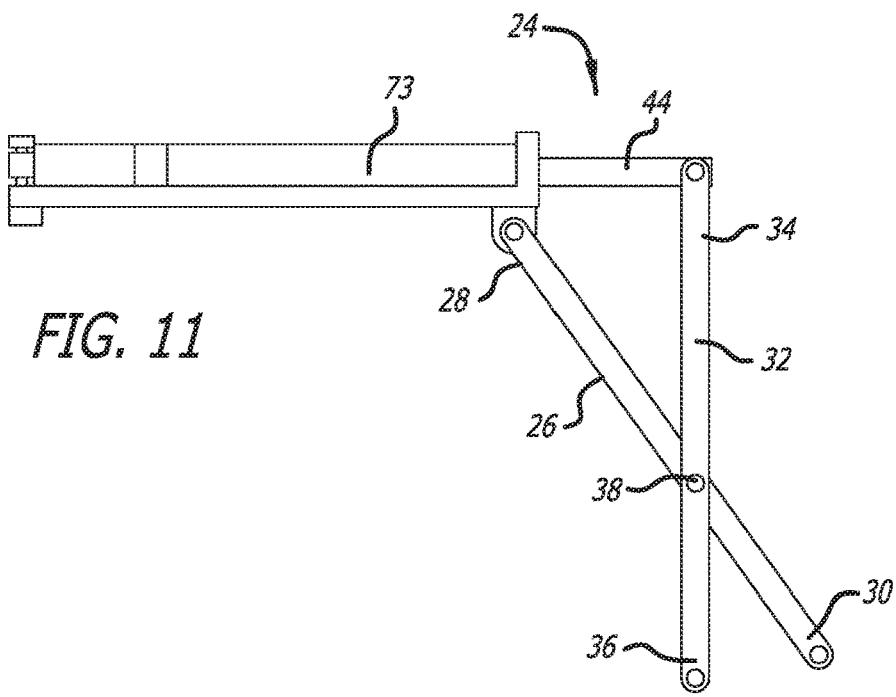
FIG. 11 is a side view of one embodiment of a compressor/distractor mechanism with a remote control actuator used in an apparatus in accordance with the invention for remotely manipulating a patient's spine.

In one preferred embodiment, referring to FIGS. 9, 10, 14A, and 14B, the remote radio frequency controller 64 controls an actuator 66, the actuator 66 including an elongated post 68 having a distal end 70. The distal end 70 defines an anterior compressor/distractor 72. The radiofrequency controller 64 remotely controls the compressor/distractor mechanism 24 located at the spinal surgical site 22 on the patient's posterior side, thereby giving the surgeon simultaneous control of posterior compression/distraction with the compressor/distraction mechanism 24, and control of anterior compression and distraction with anterior compressor/distractor mechanism 72. Referring to FIG. 11, the radio frequency controller 64 also can control the compressor/distractor mechanism 24 via an actuator 73 mounted thereon. Alternately, hand-held instruments can be used to access and manipulate the anterior spine simultaneously with remote control of posterior spine compression/distraction. Suitable hand-held instruments include, but are not limited to distracters, implant inserters, fulcrum devices, and disc preparation instruments.

Figure 12:
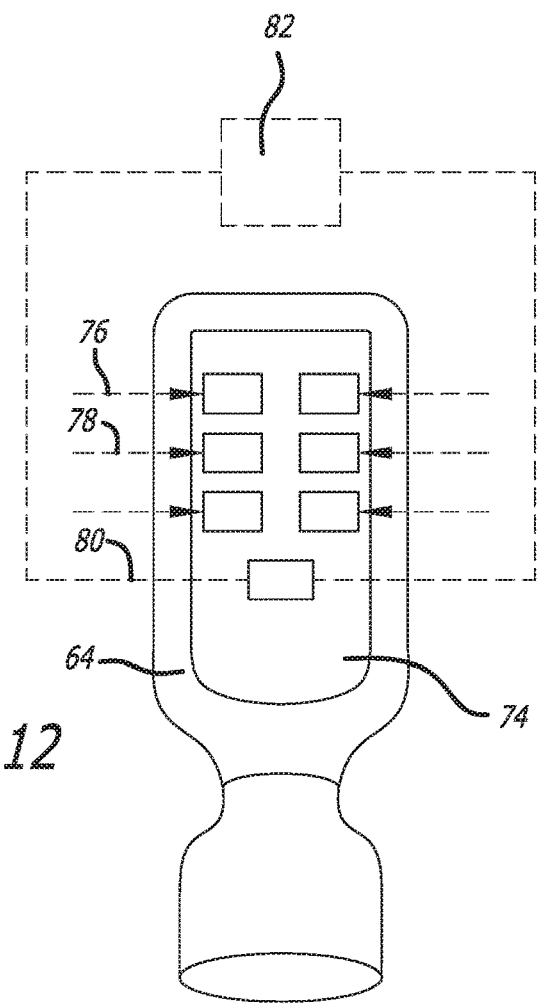
FIG. 12 is a schematic view of a radio frequency control configured to receive feedback used in an apparatus in accordance with the invention for remotely manipulating a patient's spine.

In one preferred embodiment, referring to FIG. 12, the remote radio frequency controller 64 includes a feedback device 74 adapted to receive and display feedback from one or more portions of the remote spinal manipulator 20. Feedback device 74 includes one or more of a force meter 76 displaying a force applied to the compressor/distractor mechanism 24, a strain meter 78 displaying a strain applied to the compressor/distractor mechanism 24, and a NIM meter 80 displaying impulses from a neural integrity monitoring system 82, which is well-known in the art, mounted proximate the spinal surgical site.

Alternatively, when the surgeon applies pressure to the control mechanism 46, to manipulate the patient's spine via the compressor/distractor mechanism 24, the surgeon may feel the force applied to the compressor/distractor mechanism 24 feeding back though the flexible connection portion 40 to the control mechanism 46. Alternatively, in one preferred embodiment, the radio frequency controller 64 is configured to receive haptic feedback in the form of vibrations, with the intensity of the vibrations increasing as forces on the compressor/distractor mechanism 24 increase.

Alternatively, in one preferred embodiment, the radio frequency controller 64 is configured to receive sonic feedback in the form of sound, with the pitch of the sound increasing as forces on the compressor/distractor mechanism 24 increase.

Alternatively, in one preferred embodiment, the radio frequency controller 64 is configured to receive LED scale feedback in the form of a lighted LED scale, with the brightness of the LED scale increasing as forces on the compressor/distractor mechanism 24 increase.

Alternatively, in one preferred embodiment, the radio frequency controller 64 is configured to receive alphanumeric feedback in the form of text on a screen, with the intensity of data displayed on a screen increasing as forces on the compressor/distractor mechanism 24 increase.

In one preferred embodiment, the compressor/distractor mechanism 24 is replaced by a rotational surgical table 84. Referring to FIGS. 5-8, the surgical table 84 is configured to adjust an orientation of the patient's spine, including compressing and distracting the patient's spine, and angulating a lower half of the patient's body relative to an upper half of the patient's body. The surgical table 84 also is configured to rotate, thereby providing a plurality of orientations of the table and the patient relative to a horizontal reference plane, and to simplify access to the spinal surgical site via several possible approaches. A suitable surgical table is disclosed in U.S. application Ser. No. 15/239,256, filed Aug. 17, 2016, the contents of which are incorporated herein by reference.

Figure 13A:
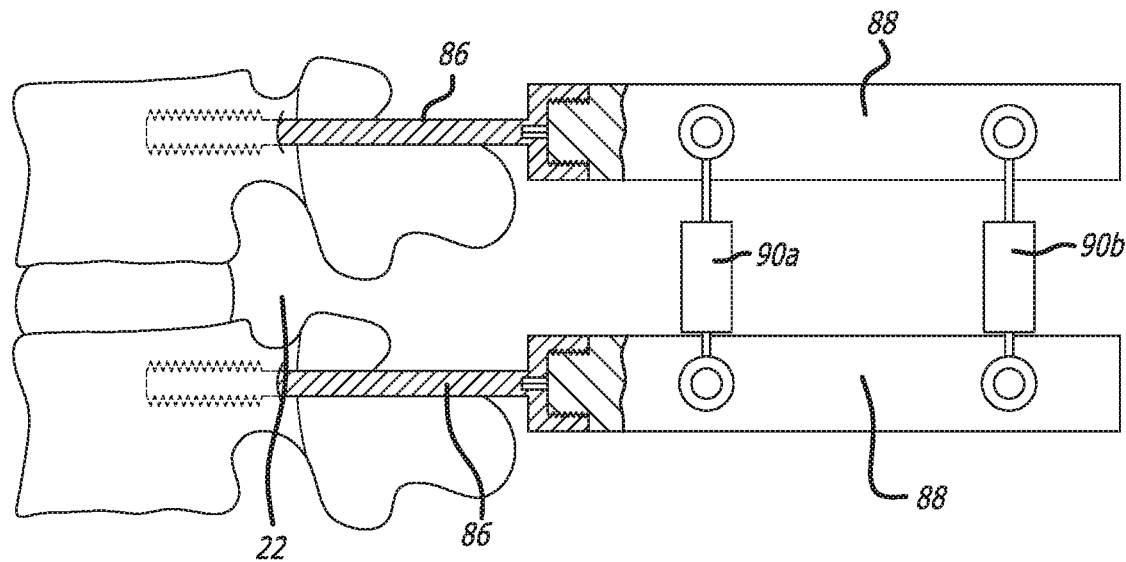
FIG. 13A is a side cross-sectional view of a posterior approach to the spinal surgical site with vertebral screws inserted into adjacent vertebrae, extenders, and extender compressor/distractor actuators used in an apparatus in accordance with the invention for remotely manipulating a patient's spine, with the actuators in an unextended position.
Figure 13B:
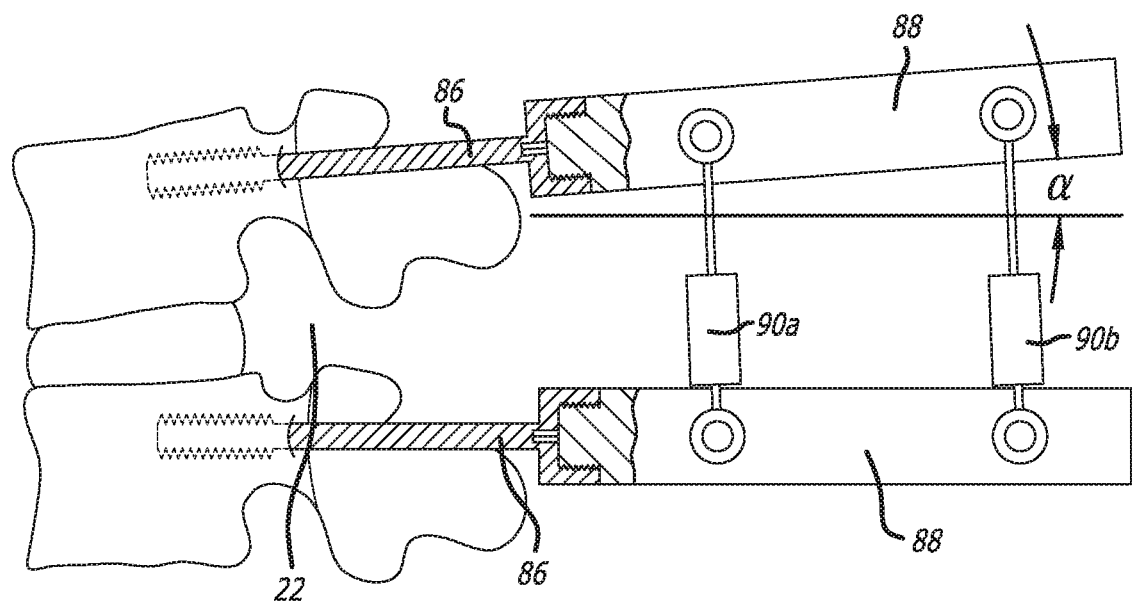
FIG. 13B is a side cross-sectional view of a posterior approach to the spinal surgical site with vertebral screws inserted into adjacent vertebrae, extenders, and extender compressor/distractor actuators, used in an apparatus in accordance with the invention, for remotely manipulating a patient's spine, with the actuators in an extended position.

In one preferred embodiment, a different configuration of a compressor/distractor mechanism adjusts both distraction and angle of the adjacent vertebrae by adjusting a distraction and an angle between vertebral screws 86 implanted in the two adjacent vertebrae. Referring to FIGS. 13A and 13B, extenders 88 are attached to distal ends of the vertebral screws 86. Initially, the vertebral screws 86 in one preferred embodiment are parallel to one another, and the extenders 88 are parallel to one another. In an alternative preferred embodiment, vertebral screws 86 defining an initial spacing and an initial angle between the connectors and the initial spacing and the initial angle between at least the connectors is altered. One or more compressor/distractor actuators 90$a$ and 90$b$ are connected to each extender 88 at selected spaced-apart locations. A displacement can be applied at each selected location, controlling resultant displacement amounts individually or simultaneously. Referring to FIG. 13B, increased displacement by compressor/distractor actuator 90$b$ at a distal end of extenders 88 increases a distance between the distal ends of the extenders 88, and defines an acute angle α between the extenders 88.

Figure 14A:
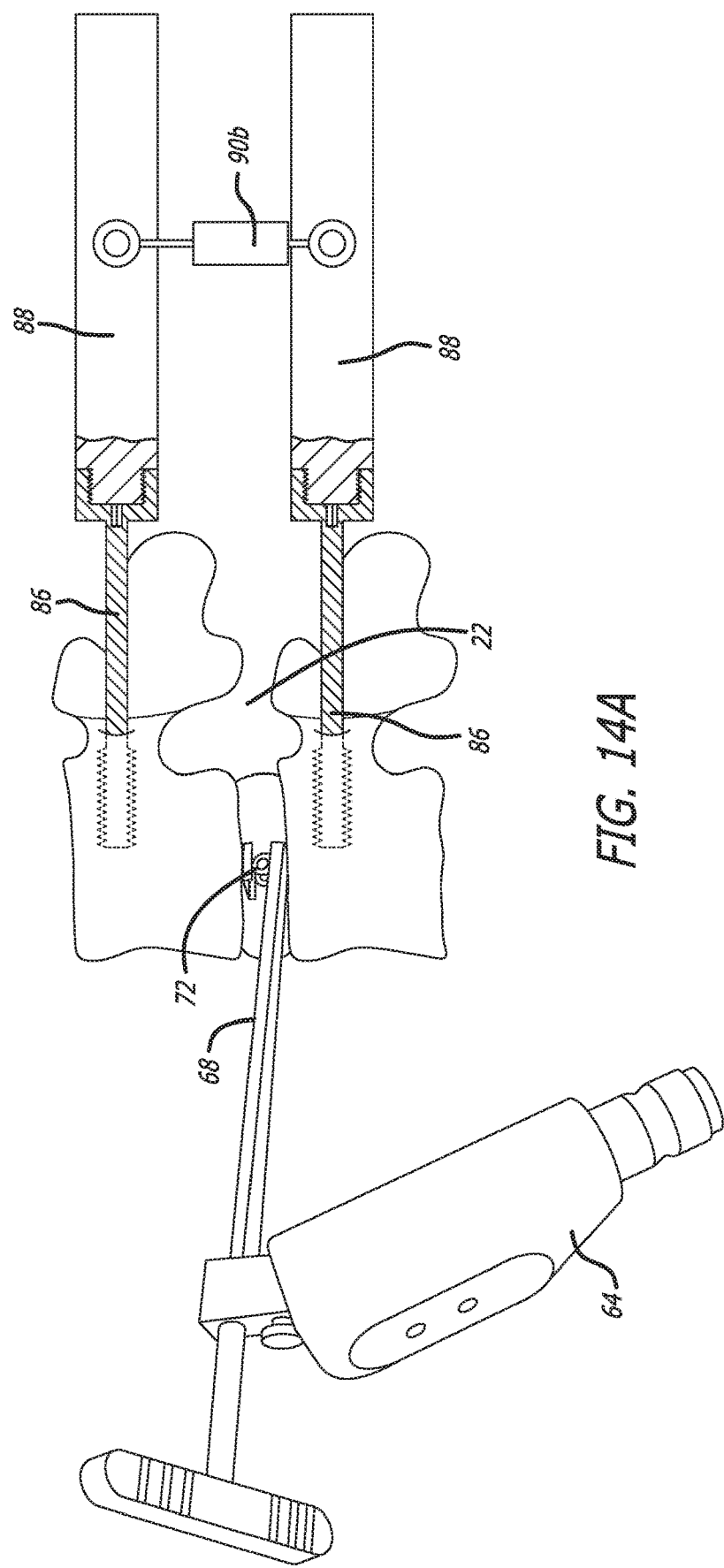
FIG. 14A is a perspective view, partly in cross-section of a posterior approach and a simultaneous anterior approach to the spinal surgical site with a radio frequency controller, an anterior compressor/distractor in an unextended position, vertebral screws inserted into adjacent vertebrae, extenders, and an extender compressor/distractor actuator, used in an apparatus in accordance with the invention, for remotely manipulating a patient's spine, with the extender compressor/distractor actuator in an unextended position.
Figure 14B:
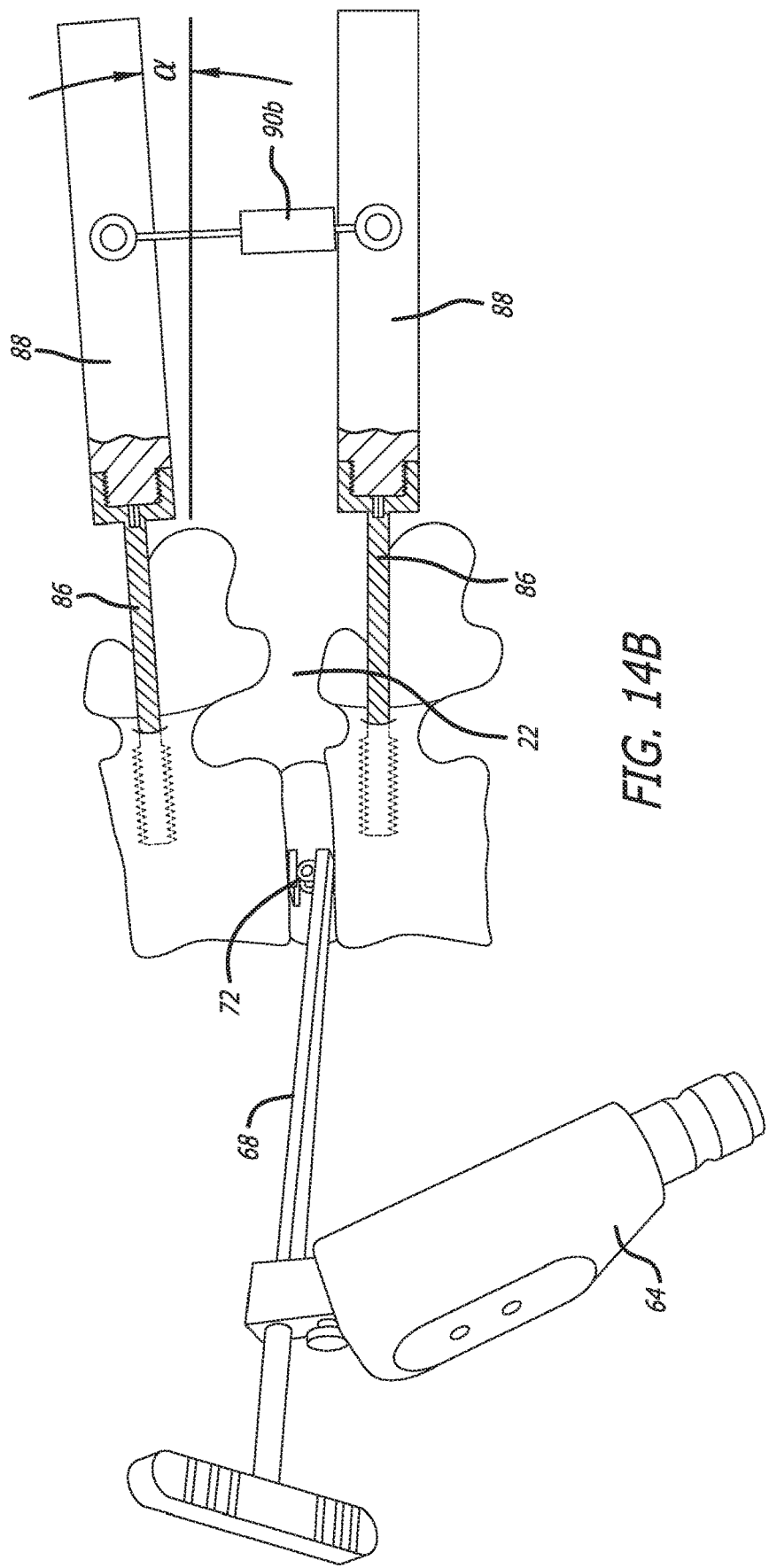
FIG. 14B is a perspective view, partly in cross-section of a posterior approach and a simultaneous anterior approach to the spinal surgical site with a radio frequency controller, an anterior compressor/distractor in an extended position, vertebral screws inserted into adjacent vertebrae, extenders, and an extender compressor/distractor actuator, used in an apparatus in accordance with the invention, for remotely manipulating a patient's spine, with the extender compressor/distractor actuator in an extended position.

In one preferred embodiment, a radio frequency controller 64, as depicted in FIGS. 14A and 14B, is provided to manipulate the posterior compressor/distractor actuators 90$a$ and 90$b$ at the patient's posterior side of the patient' spine, while the anterior compressor/distractor 72 permits the surgeon to simultaneously manipulate the anterior side of the patient's spine.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A spinal manipulating assembly for manipulating a patient's spine at a spinal surgical site in the patient, the spinal manipulating assembly comprising:
a compressor/distractor mechanism including a base portion, a first elongated arm, and a second elongated arm, each of the first elongated arm and the second elongated arm having a central portion, a proximal end portion, and a distal end portion, the central portions of the first elongated arm and the second elongated arm being pivotally attached to one another, the proximal end portion of the first elongated arm being pivotally attached relative to the base portion, and the distal end portions of the first elongated arm and the second elongated arm being configured to be attached to one of spinal anatomy and vertebral screws located on adjacent vertebrae at the spinal surgical site;
a flexible connection portion having a length, a proximal end, a distal end, and a distal end portion, the distal end portion of the flexible connection portion being moveable inwardly and outwardly with respect to the base portion of the compressor/distractor mechanism, the distal end portion of the flexible connection portion being pivotally attached to the proximal end portion of the second elongated arm of the compressor/distractor mechanism; and
a control mechanism operatively connected to the proximal end of the flexible connection portion, the control mechanism being configured to manipulate the flexible connection portion to move the flexible connection portion inwardly and outwardly with respect to the base portion of the compressor/distractor;
wherein the spinal anatomy includes at least one of lamina, posterior processes, and transverse processes, and vertebral bodies on the adjacent vertebrae at the spinal surgical site; and
wherein movement inwardly of the distal end portion of the flexible connection relative to the base portion pivots the second elongated arm relative to the first elongated arm to move the distal end portions of the first elongated arm and the second elongated arm toward one another, movement outwardly of the distal end portion of the flexible connection relative to the base portion pivots the second elongated arm relative to the first elongated arm to move the distal end portions of the first elongated arm and the second elongated arm away from one another, the movement of the distal end portions of the first elongated arm and the second elongated arm toward one another compresses the adjacent vertebrae at the spinal surgical site, and the movement of the distal end portions of the first elongated arm and the second elongated arm away from one another distracts the adjacent vertebrae at the spinal surgical site.

2. The assembly of claim 1, wherein the flexible connection portion includes an outer cable and an inner cable, the distal end portion of the flexible connection portion moveable relative to the base portion of the compressor/distractor is part of the inner cable extending through the outer cable, and the control mechanism includes a hinged lever configured, upon compression thereof, to move the distal end portion of the inner cable inwardly relative to the base portion of the compressor/distractor mechanism and the outer cable of the flexible connection portion.

3. The assembly of claim 2, wherein the hinged lever of the control mechanism is further configured, upon expansion thereof, to move the distal end portion of the inner cable outwardly relative to the base portion of the compressor/distractor mechanism and the outer cable of the flexible connection portion.

4. The assembly of claim 1, wherein one of the distal end portions of the first elongated arm and the second elongated arm is configured to attach to the one of the vertebral screws and the spinal anatomy on the adjacent vertebrae at the spinal surgical site.

5. The assembly of claim 1, wherein the flexible connection portion includes at least one of a cable, a hydraulic hose, a pneumatic hose, and an electric wire.

6. The assembly of claim 1, wherein the control mechanism includes a remote radio-frequency controller.

7. The assembly of claim 6, wherein the remote radio-frequency controller is adapted to control an actuator attached to the compressor/distractor mechanism, the actuator being configured to operate the compressor/distractor mechanism via movement of the distal end portion of the flexible connection portion.

8. The assembly of claim 6, wherein the remote radio-frequency controller includes a feedback device.

9. The assembly of claim 8, wherein the feedback device includes one of a force meter displaying a force applied to the compressor/distractor mechanism, a strain meter displaying a strain applied to the compressor/distractor mechanism, a distance meter displaying an amount of one of compression and distraction of the adjacent of the adjacent vertebrae at the surgical site, and a NIM meter displaying impulses from a neural integrity monitoring system.

10. The assembly of claim 1, wherein the compressor/distractor mechanism further comprises first and second extenders being substantially parallel to one another.

11. The assembly of claim 10, further comprising at least one posterior compressor/distractor actuator, the at least one posterior compressor/distractor actuator including a first end attached to the first extender, and a second end attached to the second extender, the first and second ends of the at least one compressor/distractor actuator being adapted to apply a pressure against the first and second extenders, thereby altering at least a spacing between at least the first and second extenders.

12. The assembly of claim 11 wherein the pressure applied against the first and second extenders further defines an acute angle between at least the first and second extenders.

13. A method of remotely manipulating a patient's spine at a spinal surgical site, the method comprising:
utilizing a spinal manipulating assembly comprising at least:
a compressor/distractor mechanism including a base portion, a first elongated arm, and a second elongated arm, each of the first elongated arm and the second elongated arm having a central portion, a proximal end portion, and a distal end portion, the central portions of the first elongated arm and the second elongated arm being pivotally attached to one another, the proximal end portion of the first elongated arm being attached relative to the base portion, and the distal end portions of the first elongated arm and the second elongated arm being configured to be attached to one of spinal anatomy and vertebral screws located on adjacent vertebrae at the spinal surgical site on a posterior side of the patient;

a flexible connection portion having a length, a proximal end, a distal end, and a distal end portion, the distal end portion of the flexible connection portion being moveable inwardly and outwardly with respect to the base portion of the compressor/distractor mechanism, the distal end portion of the flexible connection portion being pivotally attached to the proximal end portion of the second elongated arm of the compressor/distractor mechanism; and a control mechanism operatively connected to the proximal end of the flexible connection portion, the control mechanism being configured to manipulate the flexible connection portion to move the flexible connection portion inwardly and outwardly with respect to the base portion of the compressor/distractor.

attaching the compressor/distractor mechanism to the one of a pair of vertebral screws, and respective spinal anatomy, provided on the adjacent vertebrae at the spinal surgical site;

actuating the control mechanism to move the distal end portion of the flexible connection one of inwardly and outwardly with respect to the base portion to respectively move the distal portions of the first elongated arm and the second elongated arm toward and away from one another to respectively compress and distract the adjacent vertebrae at the spinal surgical site preparing at least one of a posterior approach, an anterior approach, a lateral approach, and an oblique approach to the spinal surgical site.

14. The method of claim 13, further comprising obtaining feedback, while manipulating the patient's spine, via a remote control, the feedback including at least one of a force being applied to the patient's spine by the surgical table, an amount of compression/distraction, haptic feedback, sound feedback, and at least one impulse from a neural integrity monitor.

15. The method of claim 13, further comprising attaching connectors to the one of the pair of vertebral screws, defining an initial spacing and an initial angle between the connectors, and applying a displacement force to at least one of the connectors with at least one actuator, thereby altering the initial spacing and the initial angle between at least the connectors.

16. The method of claim 13, further comprising manipulating the patient's spine at the spinal surgical site, with a hand-held compressor/distractor, via the one of the anterior approach, the lateral approach, and the oblique approach.

17. The method of claim 13, wherein the flexible connection portion includes an outer cable and an inner cable, the distal end portion of the flexible connection portion moveable relative to the base portion of the compressor/distractor is part of the inner cable extending through the outer cable, and the control mechanism includes a hinged lever configured, upon compression thereof, to move the distal end portion of the inner cable inwardly relative to the base portion of the compressor/distractor mechanism and the outer cable of the flexible connection portion.

18. The method of claim 17, wherein the hinged lever of the control mechanism is further configured, upon expansion thereof, to move the distal end portion of the inner cable outwardly relative to the base portion of the compressor/distractor mechanism and the outer cable of the flexible connection portion.

19. A spinal manipulating assembly comprising:

a compressor/distractor mechanism including a base portion, a first elongated arm, and a second elongated arm, each of the first elongated arm and the second elongated arm having a central portion, a proximal end portion, and a distal end portion, the first elongated arm and the second elongated arm being pivotally attached to one another, the proximal end portion of the first elongated arm being pivotally attached relative to the base portion;

a flexible connection portion having a length, a proximal end, a distal end, and a distal end portion, the distal end portion of the flexible connection portion being moveable inwardly and outwardly with respect to the base portion of the compressor/distractor mechanism, the distal end portion of the flexible connection portion being pivotally attached to the proximal end portion of the second elongated arm of the compressor/distractor mechanism; and a control mechanism operatively connected to the proximal end of the flexible connection portion, the control mechanism being configured to manipulate the flexible connection portion to move the flexible connection portion inwardly and outwardly with respect to the base portion of the compressor/distractor;

wherein inward movement of the distal end portion of the flexible connection relative to the base portion pivots the second elongated arm relative to the first elongated arm to move the distal end portions of the first elongated arm and the second elongated arm in a first direction, outward movement of the distal end portion of the flexible connection relative to the base portion pivots the second elongated arm relative to the first elongated arm to the move the distal end portions of the first elongated arm and the second elongated arm in a second direction.

20. The assembly of claim 19, wherein the control mechanism includes a hinged lever configured, upon compression thereof, to move the distal end portion of the flexible connection portion inwardly relative to the base portion of the compressor/distractor mechanism, and configured, upon expansion thereof, to move the distal end portion of the flexible connection portion outwardly relative to the base portion of the compressor/distractor mechanism.

* * * * *